United States Patent [19]

Parker

[11] 4,091,225

[45] May 23, 1978

[54] ANTIOXIDANT ESTER SUBSTITUTED PHENOLS AND PROCESS FOR THEIR PREPARATION

[75] Inventor: Dane K. Parker, Canton, Ohio

[73] Assignee: The Goodyear Tire & Rubber Company, Akron, Ohio

[21] Appl. No.: 435,568

[22] Filed: Jan. 22, 1974

[51] Int. Cl.$^2$ ............... C07C 69/54; C07C 69/16; C07C 69/28

[52] U.S. Cl. .................. 560/20; 560/50; 560/106; 560/217; 560/221; 560/228; 560/234; 560/254; 260/600 R; 260/611 R; 260/410.5; 260/45.85 E; 260/45.85 R; 568/734; 568/744; 568/772; 568/763

[58] Field of Search ........ 260/486 R, 476 R, 488 CD, 260/410.5, 600, 611 R, 624 R, 471 R; 560/20, 106, 217, 221, 228, 234, 50, 236, 254

[56] References Cited

U.S. PATENT DOCUMENTS

| | | | |
|---|---|---|---|
| 2,683,721 | 7/1954 | Schlesinger et al. | 260/618 X |
| 2,822,348 | 2/1958 | Haslam | 260/75 |
| 3,085,003 | 4/1963 | Morris | 260/621 K X |
| 3,116,305 | 12/1963 | Morris et al. | 260/410.5 |
| 3,644,482 | 2/1972 | Dexter et al. | 260/473 R |
| 3,649,667 | 3/1972 | Song et al. | 260/473 S |

FOREIGN PATENT DOCUMENTS

| | | |
|---|---|---|
| 817,837 | 7/1974 | Belgium. |
| 1,283,103 | 7/1972 | United Kingdom. |

OTHER PUBLICATIONS

Ibbotson et al., Chemical Abstracts vol. 75, 118934j (1971).
Nikiforov et al., Chemical Abstracts, vol. 69, 58,916u (1968).
Dietl et al., Tetrahedron Letters, 1973, No. 15, pp. 1273–1275, Apr. 1973.
American Home Products Corp., Chemical Abstracts, vol. 70, 87,262d (1969).
Neureiter, J. Organic Chemistry, 28, pp. 3486–90 (1963).
Bergmann et al., Chemical Abstracts, vol. 53, 7115g (1959).
March, Advanced Organic Chemistry; Reactions, Mechanisms & Structure, McGraw Hill Book Co. (1968), pp. 298–301 & 357.
House, Modern Synthetic Reactions, 2nd ed. W. A. Benjamin, Inc. (1972), pp. 595–596, 602.
Ingold, Structure & Mechanism in Organic Chemistry, p. 407.
Gould, Mechanisms & Structure in Organic Chemistry (1959), pp. 234–235.

*Primary Examiner*—Donald G. Daus
*Assistant Examiner*—Diana G. Ribers
*Attorney, Agent, or Firm*—J. A. Rozmajzl

[57] ABSTRACT

This invention comprises an alkylation, reduction and transesterification process for the preparation of ester substituted phenols. The products are useful as antioxidants and may be prepared in high yields and with a high degree of purity.

9 Claims, No Drawings

ANTIOXIDANT ESTER SUBSTITUTED PHENOLS AND PROCESS FOR THEIR PREPARATION

The present invention relates to the preparation of ester substituted phenols that have a stabilizing effect on oxidizable organic materials when such materials are exposed to oxidative degradative conditions. More particularly, the invention relates to the preparation of these materials by a process involving steps of alkylation, reduction and transesterification; to the materials produced by the process; and to organic materials stabilized with these materials.

Esters of the type of the present application are currently prepared by reacting starting materials such as methacryloyl chloride and alcohol. Reactions using these acid chlorides are corrosive and require the use of special equipment such as glass-lined reactors.

It is an object of the present invention to provide a process for manufacturing ester substituted phenols. It is a further object of this invention to provide compounds which lessen or minimize deterioration that usually accompanies the exposure of organic materials to oxidative conditions. Further objects will become apparent to those skilled in this art as the description proceeds.

The materials of the invention are prepared by reacting β-mono-alkyl substituted aldehydes with benzyl chloride substituted hindered phenolic compounds in a solvent such as benzene in the presence of a base acting as a catalyst to produce an aldehyde, reducing this aldehyde to form the corresponding alcohol and converting the alcohol into an ester. The process can be carried out either batchwise or continuously.

The process can be illustrated schematically by the following equations. Compounds having the general formula

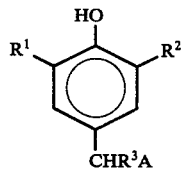

and 3,5-di-isopropyl-4-hydroxybenzyl chloride are reacted with compounds having the general formula

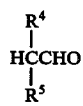

and cyclohexanecarboxaldehyde in the presence of a base acting as a catalyst while dissolved in benzene or similar solvent. The temperature of the reaction is limited by the boiling point of the solvent used. Normally, the temperature is from about 40° C to about 140° C, but the preferred temperature is from about 50° C to about 60° C. Representative examples of solvents useful in the practice of this invention are benzene, toluene, xylene and cyclohexane. The reaction forms an aldehyde having the structural formula

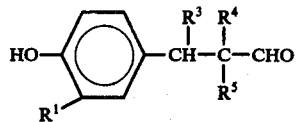

This product is reduced to form an alcohol of the general formula

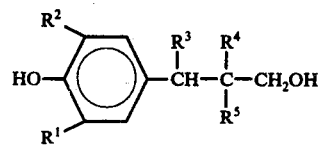

Compound (IV) is then reacted under ester interchange conditions with a compound having the general structural formula

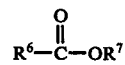

and methyl methacrylate and methyl acrylate in the presence of a catalyst to yield an ester having the structural formula

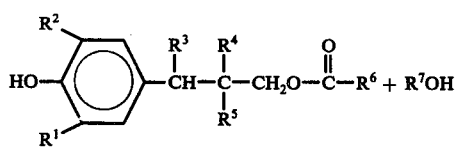

Although the compounds react in only a 1:1 molar ratio, an excess of either compound over the other can be used to insure that the reaction goes to completion. Usually, a molar ratio of from 1:1 to 1:5 is used. The molar ratio of from 1:1 to 1:3 is more preferred.

In the structural formulas above, $R^1$ and $R^2$ are the same or different radicals selected from the group consisting of tertiary alkyl radicals having from 4 to 12 carbon atoms, $R^3$ is selected from the group consisting of hydrogen and n-alkyl radicals having from 1 to 20 carbon atoms, A is a halogen selected from the group consisting of chloro, bromo and $R^4$ and $R^5$ are the same or different radicals selected from the group consisting of alkyl radicals having from 1 to 10 carbon atoms, aralkyl radicals having from 7 to 15 carbon atoms, alkenyl radicals having from 2 to 10 carbon atoms, and aryl radicals having from 6 to 12 carbon atoms, $R^6$ is selected from the group consisting of hydrogen, alkyl radicals having from 1 to 17 carbon atoms, aralkyl radicals having from 7 to 12 carbon atoms, and aryl radicals having the general formula

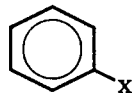

wherein X is selected from the group consisting of amino, nitro, chlor, iodo, alkoxy and alkyl radicals having from 1 to 17 carbon atoms and wherein $R^7$ is an alkyl radical having from 1 to 10 carbon atoms.

Representative examples of radicals described above are tertiary radicals such as tertiary butyl, tertiary hexyl and tertiary decyl; alkyl radicals such as methyl, ethyl, propyl, butyl, nonyl, decyl, tetradecyl, hexadecyl, nonadecyl; alkenyl radicals such as 1-propenyl and 2-butenyl; aralkyl radicals such as methyl phenyl and pentyl phenyl, and aryl radicals such as phenyl and naphthyl.

Representative examples of the Group I compounds are
3,5-di-t-butyl-4-hydroxy-benzyl chloride,
3,5-di-t-butyl-4-hydroxy-benzyl bromide,
α-methyl-3,5-di-t-butyl-4-hydroxy-benzyl chloride,
α-isopropyl-3,5-di-t-butyl-4-hydroxy-benzyl chloride
α-ethyl-3,5-di-t-butyl-4-hydroxy-benzyl bromide,
3,5-di-t-hexyl-4-hydroxy-benzyl chloride, and
3,5-di-isopropyl-4-hydroxy-benzyl chloride.

Representative examples of Group II aldehydes are
isobutyraldehyde,
2-phenyl propionaldehyde,
2-ethyl hexanal,
2-ethyl butyraldehyde,
cyclohexanecarboxaldehyde, and
2-methyl butyraldehyde.

Representative examples of Group III aldehydes are
2,2-dimethyl-3-(3,5-di-t-butyl-4-hydroxyphenyl)-propanal,
2,2-dipropyl-3-(3,5-di-t-butyl-4-hydroxyphenyl)-propanal,
2-ethyl-2-n-butyl-3-(3,5-di-t-butyl-4-hydroxyphenyl) propanal,
2-ethyl-2-methyl-3-(3,5-di-t-butyl-4-hydroxyphenyl) propanal,
2-methyl-2-phenyl-3-(3,5-di-t-butyl-4-hydroxyphenyl)propanal, and
2,2-diethyl-3-(3,5-di-t-butyl-4-hydroxyphenyl)propanal.

Representative examples of Group IV alcohols are
2,2-dimethyl-3-(3,5-di-t-butyl-4-hydroxyphenyl)-propanol,
2-ethyl-2-methyl-3-(3,5-di-t-butyl-4-hydroxyphenyl)-propanol,
2-ethyl-2-n-butyl-3-(3,5-di-t-butyl-4-hydroxyphenyl)-propanol,
2-methyl-2-phenyl-3-(3,5-di-t-butyl-4-hydroxyphenyl)propanol,
2-methyl-2-n-butyl-3-(3,5-di-t-butyl-4-hydroxyphenyl)propanol, and
2,2-diethyl-3-(3,5-di-t-butyl-4-hydroxyphenyl)-propanol.

Representative examples of Group V compounds capable of forming esters are
methyl methacrylate,
methyl benzoate,
methyl acrylate,
methyl isobutyrate,
ethyl acetate,
methyl acetate,
methyl p-aminobenzoate,
methyl p-chlorobenzoate,
methyl p-methoxybenzoate,
methyl p-nitrobenzoate, and
methyl p-methylbenzoate.

Representative ester interchange catalysts are materials selected from the group consisting of titanium esters and alcohols esters as described in U.S. Pat. No. 2,822,348. Preferred catalysts are pH neutral because of the sensitivity of the $R^1$ and $R^2$ groups to acid conditions and heat and include but are not restricted to tetraisopropyl titanate, tetrabutyl titanate and polyisopropyl titanate.

Representative examples of Group VI compounds, esters functioning as antioxidants are
2,2-dimethyl-3-(3,5-di-t-butyl-4-hydroxyphenyl)propyl methacrylate,
2,2-dimethyl-3-(3,5-di-t-butyl-4-hydroxyphenyl)propyl isobutyrate,
2,2-dimethyl-3-(3,5-di-t-butyl-4-hydroxyphenyl)propyl benzoate,
2-ethyl-2-n-butyl-3-(3,5-di-t-butyl-hydroxyphenyl)propyl methacrylate,
2-ethyl-2-n-butyl-3-(3,5-di-t-butyl-hydroxyphenyl)p-chlorobenzoate,
2-methyl-2-phenyl-3-(3,5-di-t-butyl-4-hydroxyphenyl)propyl acetate, and
2-methyl-2-phenyl-3-(3,5-di-t-butyl-hydroxyphenyl)-propyl acrylate.

The base catalyst is most effective when a catalytic amount of a quaternary ammonium hydroxide or halide is used in conjunction with excess sodium hydroxide or potassium hydroxide in a two phase system. Representative of such catalysts are
sodium hydroxide,
potassium hydroxide,
benzyl trimethyl ammonium hydroxide,
tetra-n-butyl ammonium bromide,
hexadecyl trimethyl ammonium bromide,
tetra-n-propyl ammonium bromide, and.

Esters prepared by the processes of this invention hve antioxidant properties and are capable of stabilizing polymers normally subject to oxidative degradation when incorporated into the polymers using conventional techniques such as by addition to polymer latices, or by addition to solid polymers on a mill or in a Banbury.

Various polymers subject to deterioration by oxidation can be conveniently protected by the antioxidants described herein including substituted and unsubstituted, saturated and unsaturated, natural and synthetic polymers. Oxidizable natural polymers include natural rubber in its various forms such as pale crepe and smoked sheet, balata and gutta percha. Oxidizable synthetic polymers are polymers such as those prepared from a single monomer and known as homopolymers or those prepared from a mixture or two or more copolymerizable monomers and are known as copolymers. The monomers so copolymerized may be substituted or unsubstituted, and may possess one or more double bonds, for example, diene monomers both conjugated and nonconjugated, and monolefins including cyclic and acylic monolefins, especially vinyl and vinylidene polymers. Representative examples of conjugated dienes are 1,3-butadiene, chloroprene, isoprene, 2-methyl-1,3-butadiene, 2,3-dimethyl-1,3-butadiene and piperylene. Representative examples of nonconjugated dienes are 1,4-pentadiene, 1,5-hexadiene, 1,4-hexadiene, 1,5-cyclooctadiene, dicyclopentadiene and ethylene norbornene.

Representative examples of acyclic monoolefins are ethylene, propylene, 1-butene isobutylene, 1-pentene and 1-hexene. Representative examples of cyclic monoolefins are cyclohexene, cycloheptene, cyclopentene, cyclooctene, 4-methyl cyclooctene. Representative examples of vinyl monomers are styrene, acrylonitrile, acrylic acid, ethyl actylate, butyl actylate, methyl vinyl ether, vinyl acetate and vinyl pyridine. Representative examples of vinylidene monomers are α-methyl styrene, methyl methacrylic acid, methyl methacrylate, ethyl methacrylate, glycidyl methacrylate, and vinylidene chloride.

Representative examples of synthetic polymers which can be protected by the antioxidants of this invention are polychloroprene, homopolymers of conjugated 1,3-dienes such as polyisoprene and polybutadienes having essentially all of their repeat units combined in a cis-1,4-structure, copolymers of a conjugated 1,3-diene such as isoprene and butadiene with up to 50 percent by weight of at least one copolymerizable monomer including ethylenically unsaturated monomers such as styrene or acrylonitrile, butyl rubber which is a polymerization product of a major proportion of a monoolefin and a minor proportion of a multiolefin such as butadiene or isoprene, polyurethanes containing carbon to carbon double bonds and polymer and copolymers of monoolefins containing little or no unsaturation such as polypropylene, ethylene propylene copolymers, polyethylene, and terpolymers of ethylene, propylene and a nonconjugated diene such as 1,4-hexadiene, ethylene norbornene, methylene norbornene and dicyclopentadiene.

The amount of antioxidant used to stabilize polymers can vary widely. Generally from .01 to 10 parts by weight of the antioxidant per 100 parts by weight of the polymer will be used. In unsaturated polymers, the amount used will generally range from .10 to 5.0 parts by weight based on the weight of the polymer used. A more preferred range would be from 0.5 to 2.0 parts by weight based on the weight of the polymer used. Mixtures of these antioxidants can be used if desired.

When the esters of this invention are derived from an unsaturated compound such as ethyl acrylate, the antioxidant contains ethylenic unsaturation and can be copolymerized into the polymer chain forming a self-stabilized polymer. In such polymers, the antioxidant is not extractable by common solvents and washings.

When the esters are derived from saturated compounds, copolymerization is not possible. In this case, the ester is added to the polymer using conventional methods well known to those skilled in the art, such as by addition to the solid polymer on a mill or in a Banbury.

The polymer will usually contain other compounding materials such as additives and reinforcing materials used with vulcanized rubber products. Representative examples of such additives are metal oxides, reinforcing agents, pigments, fillers, softening agents, other antioxidants, plasticizing agents, vulcanization agents and the like.

The following examples illustrate the practice of the present invention. Unless otherwise indicated, all parts and percentages are by weight.

EXAMPLE I

A three-neck, three-liter flask equipped with a mechanical stirrer, thermometer and an addition funnel was charged with 80 grams of sodium hydroxide and 80 milliliters of water under a nitrogen atmosphere. The mixture was stirred until dissolved and a mixture of 450 milliliters of benzene and 12.5 milliliters of 40 percent methanolic benzyl trimethyl ammonium hydroxide was added forming a benzene-water mixture. A mixture of 383 grams of 3,5-di-t-butyl-4-hydroxy benzyl chloride and 144 grams of isobutyraldehyde was prepared and placed in the addition funnel. The benzyl chloride/isobutyraldehyde mixture was added to the mixture of benzene and water while the flask contents were vigorously stirred at a temperature of 50° C to 60° C over a two-hour period. After addition was complete, the mixture was stirred for an additional one-half hour at room temperature. The mixture was hydrolyzed with dilute hydrochloric acid until the benzene layer turned clear yellow-orange color. The benzene layer was separated and the benzene evaporated to obtain 453 grams of 2,2-di-methyl-3-(3,5-di-t-butyl-4-hydroxyphenyl)-propanol. The melting point of the product was between 72° C and 74° C after recrystalization from hexane.

EXAMPLE II

A three-neck one-liter flask equipped with a mechanical stirrer, thermometer and addition funnel was charged with 56.9 grams (.196 mole) to 2-dimethyl-3-(3,5-di-t-butyl-4-hydroxyphenyl)propanol and 250 milliliters of ethanol. The mixture was stirred into solution. To the stirred solution, 4.0 grams (.106 mole) of sodium borohydride powder reducing agent was slowly added. The excess sodium borohydride was rinsed into the solution with an additional 75 milliliters of ethanol. The solution was stirred for between 2 and 4 hours at room temperature. The salt formed was then hydrolyzed with dilute hydrochloric acid. The solution was poured into excess cold water. The product crystallized upon the addition to the water. The product was filtered and recrystallized from hexane. The product was then dried to obtain 55.7 grams of the product having a melting point between 74° C and 76° C. The yield was 97.5 percent of 2,2-dimethyl-3-(3,5-di-t-butyl-4-hydroxyphenyl)propanol.

EXAMPLE III

A three-neck one-liter flask equipped with a mechanical stirrer and distillation apparatus was charged with 87.0 grams (.298 mole), 2,2-dimethyl-3-(3,5-di-t-butyl-4-hydroxyphenyl)propanol, 300 milliliters of methyl methacrylate and 7 milliliters of tetraisopropyl titanate and stirred until solution was achieved. The solution was heated to reflux and a methanol/methyl methacrylate azeotrope was slowly distilled off. After 5 hours, 45 milliliters of distillate had been collected. The reaction mixture was cooled to room temperature and 30 milliliters of water was added to hydrolyze the catalyst. The mixture was then stirred for one hour and allowed to stand overnight. The mixture was filtered through diatomaceous earth to remove hydrolyzed catalyst. The filtrate was dried over magnesium sulfate and then refiltered. The methanol was evaporated and the residue was recrystallized from hexane. The yield of the product before recrystallization was 103.1 grams or 96 percent. The recrystallized product had a melting point between 98° C and 100° C. The product was 2,2-dimethyl-3-(3,5-di-t-butyl-4-hydroxyphenyl)propyl methacrylate.

EXAMPLE IV

A three-neck one-liter flask equipped with a mechanical stirrer, thermometer and an addition funnel was charged with 12 grams of sodium hydroxide and 12 milliliters of water while under nitrogen atmosphere. The mixture was stirred until dissolved. Seventy milliliters of benzene and 2.5 milliliters of 40 percent methanolic benzyl trimethyl ammonium hydroxide was added to the solution forming a benzene-water mixture. A mixture of 51 grams of 3,5-di-t-butyl-4-hydroxybenzyl chloride and 44 grams of 2-phenyl propionaldehyde was placed in the addition funnel. The solution was added to the benzene-water mixture which was vigorously stirred and maintained between 50° C and 60° C over a one hour period. After the addition was complete, the total mixture was stirred for an additional one-half hour at room temperature. The mixture was hydrolyzed with dilute hydrochloric acid until the benzene layer turned a clear yellow-orange color. The benzene layer was separated. The benzene was evaporated to obtain the crude product. 27.8 Grams of the product was recrystallized from hexane at −78° C. using a dry ice-acetone mixture. The product had a melting point between 87° C and 91° C. The product was 2-methyl-2-phenyl(3,5-di-t-butyl-4-hydroxyphenyl)propanal.

The examples given illustrate the invention. Example I illustrates an alkylation of a starting compound; Example II a reduction without isolation of the product of the alkylation reaction; Example III a transesterification of the product prepared in Example II; and Example IV another example having a different aldehyde as the starting material which may then be reduced and transesterified as shown in Examples II and III.

The processes of this invention when run continuously can be illustrated by the equation shown below. $R^1$, $R^2$, $R^3$, $R^4$, $R^5$, $R^6$ and $R^7$ are the same radicals as described and exemplified above.

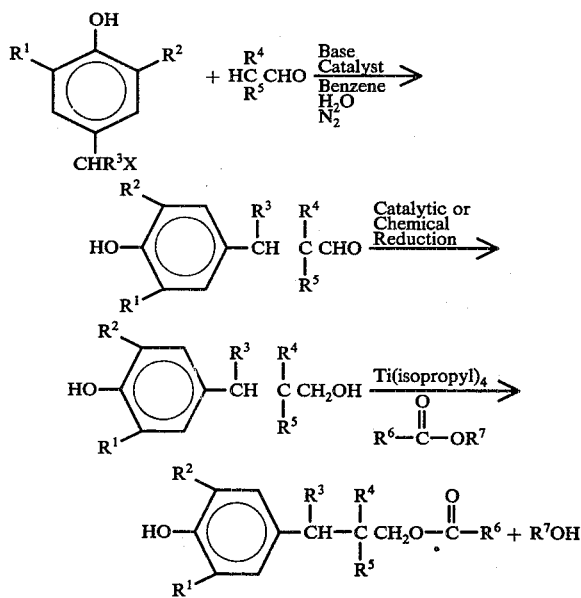

As indicated, the process can be operated as a continuous process. When operated as a continuous process, step 1 proceeds as a normal alkylation. After the formation of the aldehyde, a reduction catalyst is added to form an alcohol. Following the reduction to the alcohol, the solvent is stripped off and replaced with ester forming compound, for example, methyl methacrylate, and the transesterification catalyst for the reaction to the final product.

The transesterification product of Example III was copolymerized using emulsion polymerization techniques with monomer systems containing 75 parts of butadiene, 25 parts of styrene (SBR); 67 parts of butadiene, 33 parts of acrylonitrile (NBR); and 100 parts of butadiene (PBD) all containing 1.50 parts of the antioxidant being tested. The antioxidant control was a phenolic antioxidant, sold by The Goodyear Tire & Rubber Company as Wing-Stay L. Before oxygen absorption tests were run on the polymers, the polymers were extracted for 48 hours with methanol to remove any unreacted, free monomeric antioxidants that were present, dried again, and then dissolved in benzene. The benzene solutions were poured into aluminum trays and the solvent was allowed to evaporate. The resulting films were placed in an oxygen absorption apparatus. The amount of oxygen absorbed in a particular interval of time was determined and is listed in the following Table 1. The testing procedure is described in further detail in Industrial and Engineering Chemistry, Vol. 43, page 456 (1951) and Industrial and Engineering Chemistry, Vol 45, page 392 (1953).

Table 1

| Antioxidant | PHR | Copolymer | Hours to Absorb 1% Oxygen at 100° C |
| --- | --- | --- | --- |
| Control | 1.5 | SBR | 15 |
| Example III | 1.5 | SBR | 430 |
| Example III | 1.5 | PBD | 330 |
| Example III | 1.5 | NBR | 138 |

While certain representative embodiments and details have been shown for the purpose of illustrating the invention, it will be apparent to those skilled in this art that various changes and modifications may be made therein without departing from the spirit or scope of the invention.

What is claimed is:

1. A process comprising (a) reacting in an inert atmosphere a compound having the general structural formula

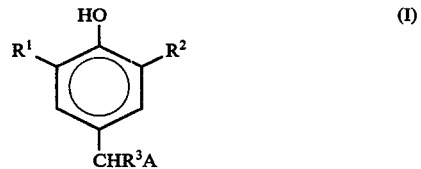

with a compound having the general formula

in the presence of a basic catalyst while dissolved in an organic solvent to yield an aldehyde having the structural formula

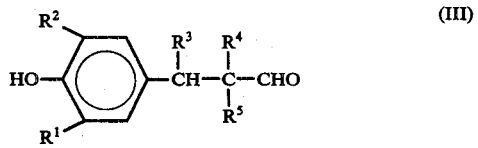

(b) separating and reducing the aldehyde to form an alcohol having the general structural formula

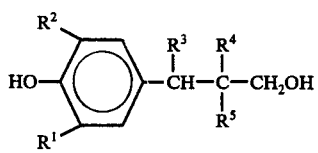
(IV)

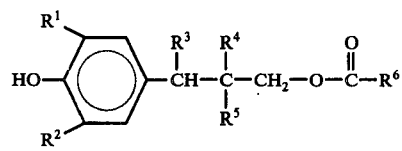

(c) separating the alcohol and reacting it with an ester forming compound selected from the group consisting of methyl acrylate, methyl methacrylate, ethyl acrylate and a compound of the general formula

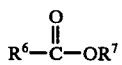
(V)

while in the presence of a transesterification catalyst to yield (d) an ester with the structural formula

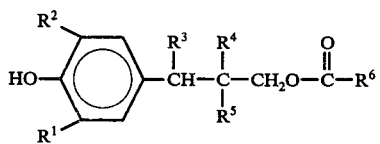
(VI)

wherein $R^1$ and $R^2$ are the same or different radicals selected from the group consisting of tertiary alkyl radicals having from 4 to 12 carbon atoms, $R^3$ is selected from the group consisting of hydrogen, methyl and ethyl, A is selected from the group consisting of chloro and bromo, $R^4$ and $R^5$ are the same or different radicals selected from the group consisting of methyl, ethyl, n-propyl and n-butyl and $R^6$ is selected from the group consisting of methyl, ethyl, propyl and butyl, aralkyl radicals having from 7 to 12 carbon atoms, vinyl, 2-propenyl and aryl radicals having the general formula

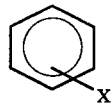

wherein X is selected from the group consisting of hydrogen, amino, nitro, chloro, bromo and alkyl radicals having from 1 to 17 carbon atoms and wherein $R^7$ is an alkyl radical having from 1 to 10 carbon atoms.

2. Compounds having the general formula wherein $R^1$ and $R^2$ are the same or different radicals selected from the group consisting of tertiary alkyl radicals having from 4 to 12 carbon atoms, $R^3$ is selected from the group consisting of hydrogen, methyl and ethyl, $R^4$ and $R^5$ are the same or different radicals selected from the group consisting of methyl, ethyl, n-propyl and n-butyl and $R^6$ is selected from the group consisting of methyl, ethyl, propyl and butyl, aralkyl radicals having from 7 to 12 carbon atoms, vinyl, 2-propenyl and aryl radicals having the general formula

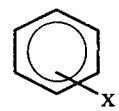

wherein X is selected from the group consisting of hydrogen, amino, nitro, chloro, bromo and alkyl radicals having from 1 to 17 carbon atoms.

3. A process as described in claim 1 wherein the solvent is selected from the group consisting of benzene, toluene, xylene and cyclohexane.

4. A process as described in claim 1 above wherein compounds having the general formula (I) are selected from the group consisting of 3,5-di-t-butyl-4-hydroxy-benzyl chloride; 3,5-di-t-butyl-4-hydroxy-benzyl bromide; α-methyl-3,5-di-t-butyl-4-hydroxy-benzyl chloride; α-methyl-3,5-di-t-butyl-4-hydroxy-benzyl bromide; and 3,5-di-t-hexyl-4-hydroxy-benzyl chloride.

5. A process as described in claim 1 above wherein compounds having the general structural formula (II) are selected from the group consisting of isobutyraldehyde; for; 2-ethyl hexanal; 2-ethyl butyraldehyde; 2-methyl butyraldehyde.

6. A process as described in claim 1 wherein compounds having the general formula (V) are selected from the group consisting of methyl methacrylate, methyl acrylate, methyl benzoate, methyl isobutyrate and ethyl acetate.

7. A process as described in claim 1 wherein the transesterification catalyst is selected from the group consisting of tetraisopropyl titanate, tetrabutyl titanate, and polyisopropyl titanate.

8. A process as described in claim 1 wherein the compound produced is 2,2-dimethyl-3-(3,5-di-t-butyl-4-hydroxy-phenyl)propyl methacrylate.

9. A process as described in claim 1 wherein the compound produced is 2,2-dimethyl-3-(3,5-di-t-butyl-4-hydroxy-phenyl)propyl acetate.

* * * * *